Figure 1:
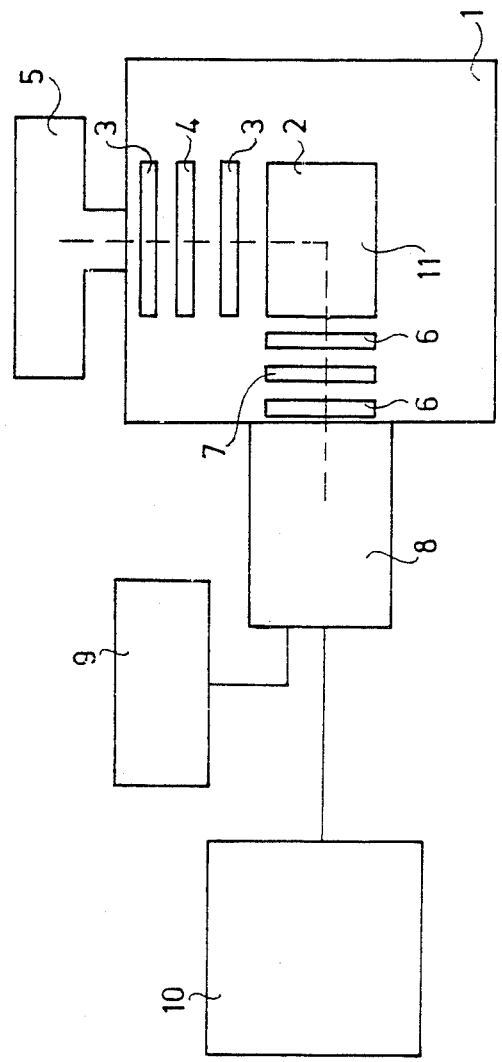

United States Patent [19]

Resli et al.

[11] Patent Number: 4,880,732
[45] Date of Patent: Nov. 14, 1989

[54] PROCESS FOR THE RAPID DETERMINATION OF SPERM CELL COUNT AND/OR LIVING SPERM COUNT

[75] Inventors: István Resli; Tibor Takács; Sándor Damjanovich; Rezso Gáspár; Lajos Trón; János Szöllősi; János Matkó, all of Debrecen, Hungary

[73] Assignee: Innofinance Altalanos Innovacios Penzintezet, Budapest, Hungary

[21] Appl. No.: 153,599

[22] Filed: Feb. 8, 1988

[51] Int. Cl.$^4$ ................................................. C12Q 1/02
[52] U.S. Cl. ............................................ 435/29; 435/4
[58] Field of Search ............................................ 435/29

[56] References Cited

U.S. PATENT DOCUMENTS 4,559,309 12/1985 Evenson et al. .................. 436/172
4,683,213 7/1987 Ax .................................... 435/806

OTHER PUBLICATIONS

Blazak et al.-Chem. Abst., vol. 97 (1982), p. 106458y.

Primary Examiner—Sam Rosen
Attorney, Agent, or Firm—Keil & Weinkauf

[57] ABSTRACT

The invention relates to a process and an equipment for the rapid determination of the spermium count of sperm samples and/or the ratio of the living spermia. The process comprises dissolving the fluorescent dyestuff propidium iodide in a buffer and measuring the intensity ($F_o$), then adding the sperm sample and, after measurement of the intensity ($F_1$) and addition of a cytoplasm membrane-permeabilizing agent, determining the intensity ($F_2$), then adding a buffer and a permeabilizing agnet to the buffer and measuring the intensity ($F_3$) and subsequently the intensity ($F_4$) of the pure buffer and finally the intensity ($F_5$) of the sperm mixture added to the buffer, and calculating the cell concentration by using the formula:

$$\text{cell concentration} = \alpha \cdot \frac{(F_2 - F_3) - (F_5 - F_4)}{F_0} \text{ million/mm}^3$$

wherein $\alpha$ is the multiplication product from the slope of the calibration curve with the predilution ratio; and calculating the living cell ratio by using the formula:

$$\text{living cell \%} = 100 - \frac{(F_1 - F_0) - (F_5 - F_4)}{(F_2 - F_3) - (F_5 - F_4)} \cdot 100.$$

3 Claims, 3 Drawing Sheets

PROCESS FOR THE RAPID DETERMINATION OF SPERM CELL COUNT AND/OR LIVING SPERM COUNT

This invention relates to a process and equipment for the rapid determination of the spermium cell count and/or the ratio of living spermia in sperm samples.

The research work connected with spermia cannot be separated from economical viewpoints, production interests of the artificial insemination and practical animal husbandry as well as the demand to increase production. Thus, a number of research programs have been directed to an objective qualification of sperm, more particularly, to the development of processes by means of which the biological utility of the sperm could be predicted in the practice.

In addition to the traditional staining techniques, several methods are available today that make it possible to observe very fine alternations of the qualitative, morphological and physiological characteristics of the sperm, such as electron microscopy [J. M. Bedford: Am. J. Anat. 123, 329 (1968); Saacke: J. Amin. Sci. 115, 143 (1964)], enzymological analysis [Acta Vet. Scand. 17, 83 (1967)] and methods based on laser techniques [Magyar Állatorvosok Lapja 38, 38 (1983); Biophys. J. 31, 147 (1983)].

In the sperm, cells in various physiological conditions are present, and the ratio of these subpopulations plays a decisive role in insemination.

Nowadays, microscopic investigation is still the most widely used routine examination method for estimating the concentration, motility and thus the ratio of living spermia. By using an appropriate enlargement and observing the spermia within the sight field, the investigator subjectively estimates the biological utility of the sperm tested on the basis of movement of the spermia. This method is inaccurate and shows an error of about 25% [Techn. Conf. Art. Ins. Reprod. Proc. p. 3 (1973)].

This qualification can be supplemented with various staining techniques. In particular, the living subpopulation can be distinguished from the dead one by using the so-called vital dyeing since the dye is not taken up by the originally living cells. The inaccurateness of this method is due to the fact that a population of several million cells is qualified on the basis of the examination of only a few hundred cells. Furthermore, this method is time-consuming and cannot be fitted to the production technology.

Another known method is based on the observation that a velocity-dependent frequency-modulated component is contained in the light scattered by the head section of spermia when the sperm sample is illuminated by the monochromatic light of a He-Ne laser. The velocity distribution of the spermia can be concluded by Fourier transformation of frequency spectrum of the Doppler signal. This method is also useful for measuring the spermium concentration (LAZYMOT device of BIG Biotechnik GmbH., Mönchengladbach, German Federal Republic, used for investigation of the motility).

On the other hand, the known methods do not assure an accurate and reproducible result and, on the other hand, they are too complicated and expensive for wide use in industrial processes for working-up of the sperm.

The aim of the present invention is to provide a process and equipment for carrying out a simple and relatively inexpensive qualification of sperm with an accuracy satisfying production requirements.

The invention is based on the recognition that the fluorescence characteristics of propidium iodide such as the spectral distribution and the quantum efficiency of fluorescence of the emitted light are altered by the interaction with and binding of the dyestuff to nucleic acids. The binding of the dyestuff molecules appears as a significant increase in the fluorescence level which is characteristic of the free dyestuff.

The sperm samples are qualified on the basis that, in contrast with the intact cells, propidium iodide is very quickly taken up by the dead cells having a membrane with enhanced permeability whereby an increase in the intensity is observed as compared to that of the free dyestuff. This is a distinctly rapid process whereby an even higher fluorescence intensity is obtained which is proportional to the total spermium count.

Thus, the present invention relates to a process for the rapid determination of the spermium cell count of sperm samples and/or the ratio of the living spermia, which comprises dissolving the fluorescent dyestuff propidium iodide in a buffer and measuring the intensity ($F_0$), then adding the sperm sample and, after measurement of the intensity ($F_1$) and addition of a cytoplasm membrane-permeabilizing agent, determining the intensity ($F_2$), then adding a buffer and a permeabilizing agent to the buffer and measuring the intensity ($F_3$) and subsequently the intensity ($F_4$) of the pure buffer and finally the intensity ($F_5$) of the sperm mixture added to the buffer, and calculating the cell concentration by using the formula:

$$\text{cell concentration} = \alpha \cdot \frac{(F_2 - F_3) - (F_5 - F_4)}{F_0} \text{ million/mm}^3$$

wherein $\alpha$ is the multiplication product from the slope of the calibration curve with the predilution ratio; and calculating the living cell ratio by using the formula:

$$\text{living cell \%} = 100 - \frac{(F_1 - F_0) - (F_5 - F_4)}{(F_2 - F_3) - (F_5 - F_4)} \cdot 100.$$

As a cytoplasm membrane-permeabilizing agent saponin, digitonin or nystatin may preferably be added to the stained cell sample whereby the membrane of each cell becomes permeable.

The invention also relates to equipment for carrying out the above process, which equipment comprises: a cuvet-holder unit (1); a light source (5) connected to it; an input-optic including an optical filter (4) and two lenses (3) which, after choosing the appropriate spectral range, project the light of the light source to the sample placed on the thermostatable cuvet-holder (2); an output-optic which is perpendicular to the axis of the input-optic and includes an optical filter (7) and two lenses (6) which, through the light detector (8) joining to the cuvet-holder unit, projects the emission of the sample (11) placed in the cuvet-holder; a high-voltage supply unit (9) for the light detector; and detecting electronics (10) receiving the signals of the light detector.

A schematic diagram of the equipment according to the invention is shown in FIG. 1.

The equipment functions as follows: The device is started up by switching on the main switch and adjusting a high voltage value on the high-voltage supply unit (9) feeding the light detector (8). The high-voltage value assures the display of an emission intensity which is easily measured with the selected amplifying field by the detecting electronics (10) receiving the signals of the light detector.

For measuring the emission intensity of the samples used for the determinations, the sample placed in the cuvet to be measured is put into the cuvet-holder (2), whereafter the emission intensity is automatically displayed by the detecting electronics (10) of the equipment.

For carrying out a complete series of measurements, i.e. for determining the living cell ratio of a sperm sample to be qualified, the emission intensity of six samples prepared in different ways has to be measured. Thereafter, the evaluation is made by determining the living cell ratio as well as the absolute cell concentration of the sample to be qualified.

The extent of amplification as well as of the filtration diminishing the electronic background noise may be varied according to several grades. Suitably, the value of the high voltage switched on the photoelectron-multiplier used as detector is made to appear on a recorder.

The main advantages of the process and equipment of the invention may be summarized as follows.

(a) They are more simple and inexpensive than any of the prior art.

(b) Accurate and reproducible results are rapidly obtained which can thus be inserted into the technology of working up the sperm.

(c) They are useful to determine the accurate ratio of the living cells to the dead ones.

(d) An objective establishment of the resistance of an optional ejaculate and conclusively the prediction of the biological value of the sperm tested are made possible by the serial examinations of sperm samples subjected to a loading test.

(e) The measurement of the absolute spermium concentration also becomes possible.

(f) The process is more sensitive than those of the prior art.

(g) On binding of the propidium iodide dyestuff, the fluorescence significantly increases, resulting in a higher resolving power.

The process of the invention is further illustrated in detail by the following non-limiting Example.

Figure 2:
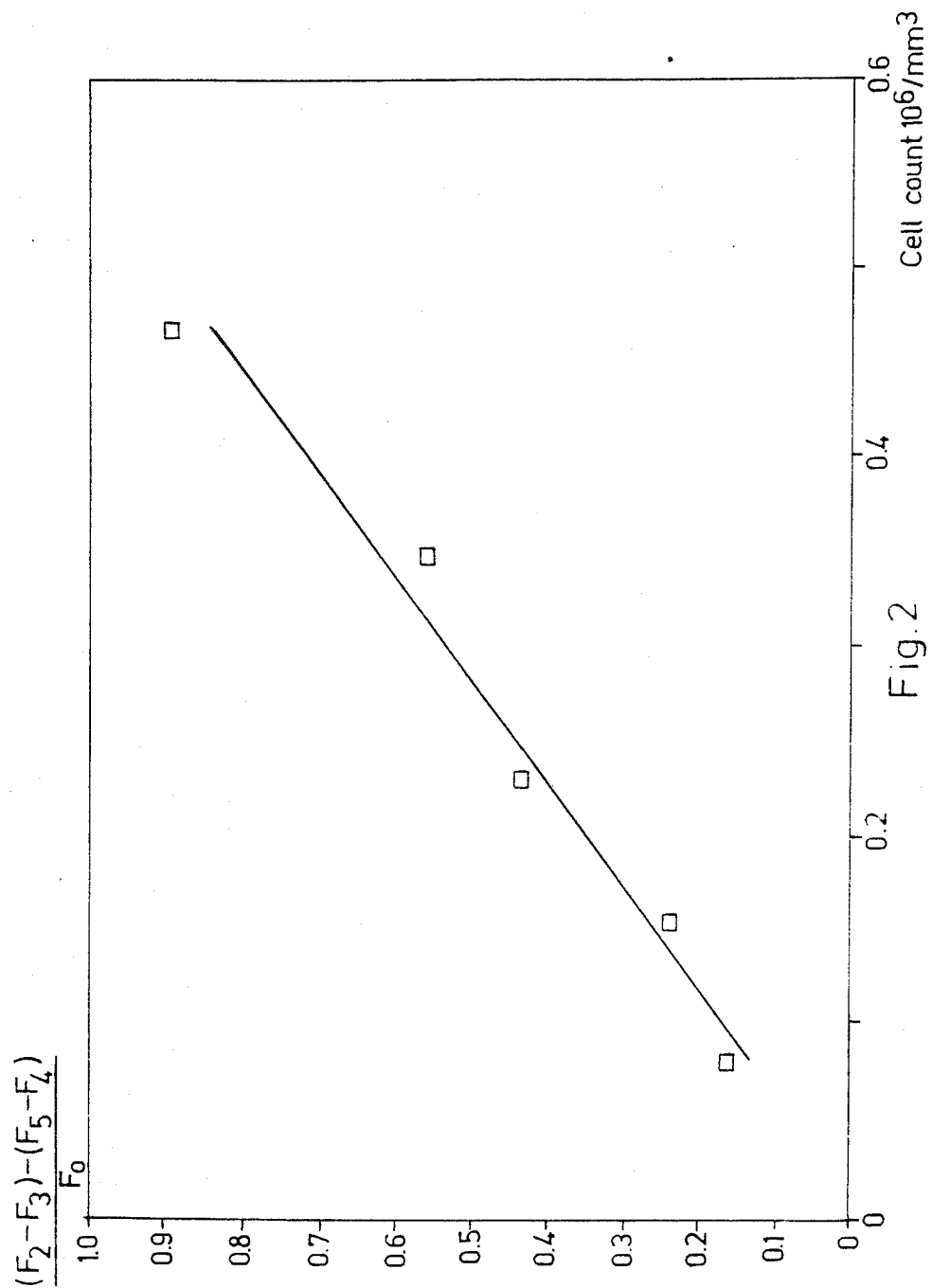
Figure 3:
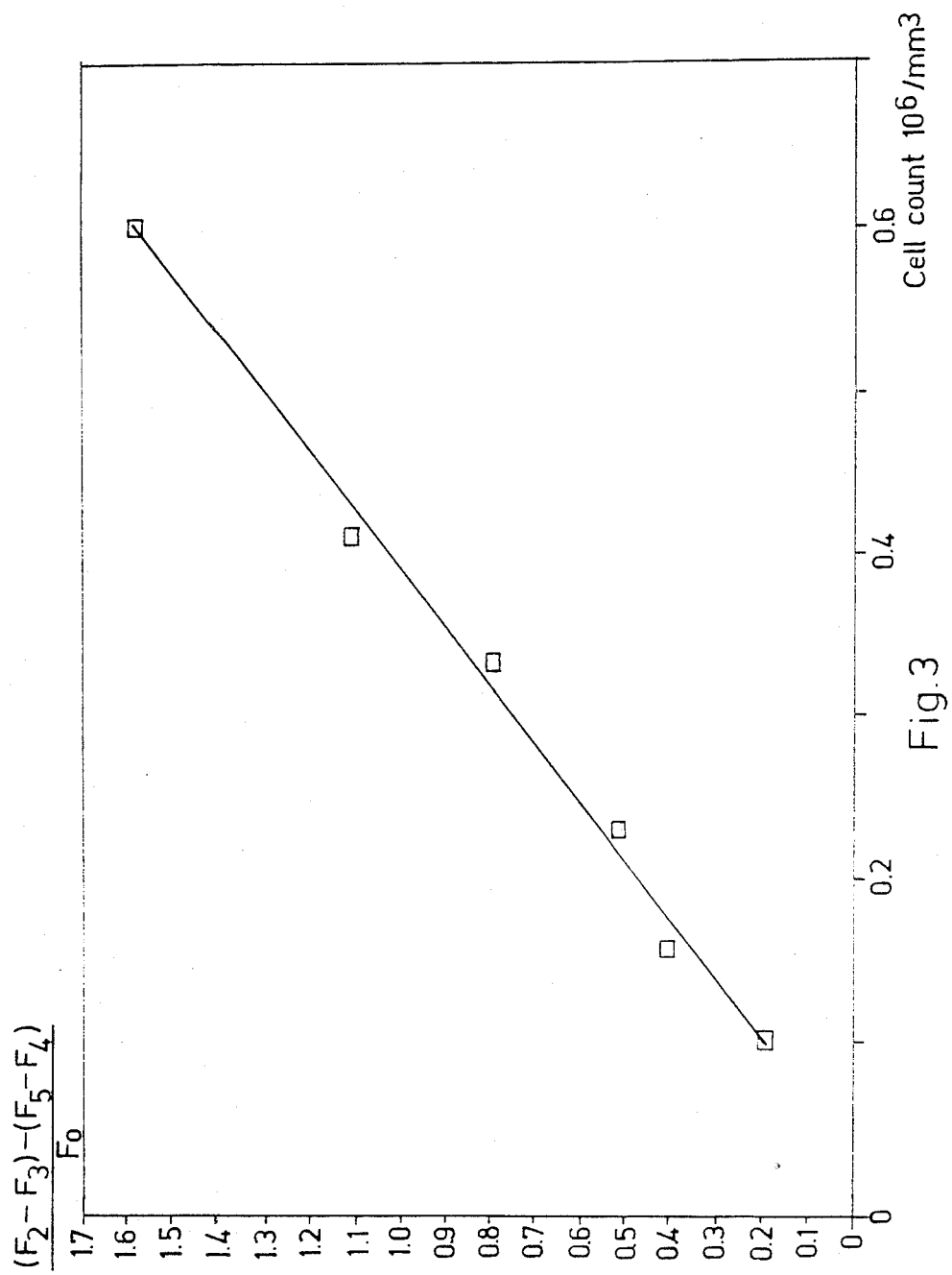

A calibration curve of boar sperm is shown in FIG. 2 and that of bull sperm in FIG. 3.

EXAMPLE

The ratio of the living cells is determined as follows.

1. The fluorescence intensity ($F_0$) of propidium iodide (PI) dissolved in a buffer is measured on 1600 $\mu$l of a dyestuff solution having 25 mg/liter concentration of PI and serving also as standard.

2. The sperm sample to be tested pre-diluted with 40 $\mu$l of the buffer is added and the intensity ($F_1$) is measured.

3. As a permeabilizing agent 40 $\mu$l of an ethanolic solution containing 5 mg/ml of digitonin are added to the cell sample and the intensity ($F_2$) is measured.

4. Instead of the sperm sample, 40 $\mu$l of PBS (phosphate buffer saline) and then the permeabilizing agent are added to the dyestuff solution, and the fluorescence intensity ($F_3$) of the thus-prepared solution is determined (1600 $\mu$l of PI solution + 40 $\mu$l of buffer + 40 $\mu$l of ethanolic digitonin solution).

5. The intensity ($F_4$) of 1600 $\mu$l of the buffer solution is measured.

6. The intensity ($F_5$) is determined after adding 40 $\mu$l of the pre-diluted sperm to the buffer.

The ratio of intact cells is calculated from the intensities measured by using the formula:

$$\text{Living cells \%} = 100 - \frac{(F_1 - F_0) - (F_5 - F_4)}{(F_2 - F_3) - (F_5 - F_4)} \cdot 100$$

The cell count is determined as follows: The cell count contained in the sample can simultaneously be determined from the intensities measured above within the serial measurements for determining the living cell ratio. Namely, the difference between the measured intensities $F_2$ and $F_3$, i.e. the value of ($F_2$–$F_3$), originates from the total permeabilized cells and therefore it is proportional to the cell count of the sample. Within the range $1 \times 10^5$ to $1.5 \times 10^6$ cell/ml the value of ($F_2$–$F_3$) shows a linear correlation to the cell concentration. Thus, within this range, by means of calibration the cell count of the sample can be obtained from the value of ($F_2$–$F_3$) measured in the course of the process. The non-specific intensity enhancement ($F_5$–$F_4$) resulting from the spermia has to be considered in this case, too.

The calculation is carried out as follows:

Spermium concentration in million/mm$^3$ =

$$\alpha \cdot \frac{(F_2 - F_3) - (F_5 - F_4)}{F_0}$$

wherein $\alpha$ has the above value.

The calibration curve can be prepared by using a flow-cytometer and a cell sample labelled with PI as follows.

The cell suspension to be tested is diluted to a concentration of $0.5 \times 10^6$ to $2 \times 10^6$ cell/ml by using PBS buffer. Under cooling with ice, 1 ml of the diluted suspension is treated with 1 ml of 1% NP-40 solution (Nonidet P-40, SIGMA, Deisenhofen, German Federal Republic). Under the effect of this treatment, all cells perish and their membranes become permeable for PI.

After this treatment, the sample is stained by adding PI dissolved in PBS buffer to a final concentration of 30 $\mu$l/ml of the dyestuff.

The stained sample is analyzed in a flow-cytometer, e.g. in a Dickinson FACS III-type device by using a flow rate of 1500 cell/sec. The excitation is achieved by an argon ion laser at 488 nm wavelength while the emission is registered by inserting a suppression filter which is surface-permeable in the range above 620 nm.

In the course of the analysis, the cells passing through the system are counted by the device on the basis of registering the fluorescence intensity of PI. Since the PI is uniformly taken up by the spermia of the sample under effect of the treatment, this count corresponds to the absolute cell count. By the accurate back-measurement of the amount of sample consumed in the measurement and considering the dilution factors, the original cell concentration of the sample is obtained which equals with the fluorescence intensity quotient $$\frac{(F_2 - F_3) - (F_5 - F_4)}{F_0}$$

measured on the same sample in a spectrofluorimeter. On preparing a dilution series from the sample and using a series of parallel cytometric and spectrofluorimetric measurements, the absolute cell counts belonging to the intensity quotient measured in the spectrofluorimeter are determined in various concentration ranges, the accuracy of which is assured by examinations repeated several times at the same points of measurements. Since the value of the quotients of the fluorescence intensities is in a linear correlation to the cell count, a regression line of the measurements for any sperm species can be plotted, on the basis of which the cell count belonging to a defined intensity quotient can be determined.

The multiplication product from the slope of the regression line with the dilution of the sperm sample tested gives the coefficient $\alpha$ which, on multiplying with the fluorescence intensity quotient measured, indicates the original cell concentration of the sample.

The callibration curve may also be constructed by haemocytometric counting.

The calculations may preferably be performed on a computer.

We claim:

1. A process for the rapid determination of the total cell concentration of a sperm sample, the living cell concentration of a sperm sample or both comprising:
   (a) dissolving the fluorescent dyestuff propidium iodine in a buffer solution to form a dyestuff solution and measuring the fluorescent intensity, $F_0$;
   (b) prediluting a sperm sample with buffer solution and adding the prediluted sperm sample to the dyestuff solution formed in step (a) and measuring the fluorescent intensity, $F_1$;
   (c) adding a cytoplasm membrane-permeabilizing agent to the solution formed in step (b) and measuring the fluorescent intensity, $F_3$;
   (d) adding to a propidium iodine dyestuff solution, as formed in step (a), an amount of buffer solution equal to the amount of prediluted sperm sample added in step (b) and a cytoplasm membrane-permeabilizing agent and measuring the fluorescent intensity, $F_4$;
   (e) measuring the fluorescent intensity, $F_5$, of a pure buffer solution;
   (f) adding the prediluted sperm sample to the pure buffer of step (e) and measuring the fluorescent intensity $F_4$
   and thereafter
   (1) calculating the total cell concentration from the equation:

$$\text{cell concentration} = \alpha \times \frac{(F_2 - F_3) - (F_5 - F_4)}{F_0} \text{ million/mm}^3$$

wherein $\alpha$ is the multiplication product from the slope of the calibration curve with the predilution ratio; and
   (2) calculating the ratio of living cells to total cell concentration from the equation:

$$\text{living cell \%} = 100 - \frac{(F_1 - F_0) - (F_5 - F_4)}{(F_2 - F_3) - (F_5 - F_4)} \times 100.$$

2. The process of claim 1, wherein the propidium iodide is used in a concentration of from 12.5 mg/liter to 25 mg/liter.

3. The process of claim 1, wherein saponin, digitonin or nystatin is used as the cytoplasm membrane-permeabilizing agent.

* * * * *